United States Patent
Köhler (10) Patent No.: US 10,046,179 B2
(45) Date of Patent: Aug. 14, 2018

(54) HIGH INTENSITY FOCUSED ULTRASOUND TARGETING

(71) Applicant: Profound Medical Inc., Mississauga (CA)

(72) Inventor: Max Oskar Köhler, Espoo (FI)

(73) Assignee: Profound Medical Inc., Mississauga, ON (CA)

( * ) Notice: Subject to any disclaimer, the term of this patent is extended or adjusted under 35 U.S.C. 154(b) by 905 days.

(21) Appl. No.: 14/406,550

(22) PCT Filed: Jun. 21, 2013

(86) PCT No.: PCT/IB2013/055091
§ 371 (c)(1),
(2) Date: Dec. 9, 2014

(87) PCT Pub. No.: WO2013/190505
PCT Pub. Date: Dec. 27, 2013

(65) Prior Publication Data
US 2015/0142034 A1   May 21, 2015

(30) Foreign Application Priority Data
Jun. 21, 2012 (EP) .................................... 12172873

(51) Int. Cl.
*A61N 7/00* (2006.01)
*A61N 7/02* (2006.01)
*A61B 5/01* (2006.01)
*A61B 5/055* (2006.01)
(Continued)

(52) U.S. Cl.
CPC ................ *A61N 7/00* (2013.01); *A61B 5/015* (2013.01); *A61B 5/055* (2013.01); *A61N 7/02* (2013.01);
(Continued)

(58) Field of Classification Search
CPC ........... A61B 2018/00577; A61B 2018/00738; A61B 2018/00791; A61B 2018/00898;
(Continued)

(56) References Cited

U.S. PATENT DOCUMENTS 7,367,944 B2   5/2008   Rosemberg
7,657,299 B2   2/2010   Huizenga et al.
(Continued)

FOREIGN PATENT DOCUMENTS

EP   0627206 A2   12/1994
EP   2455133 A1   5/2012
(Continued)

OTHER PUBLICATIONS

Mougenot, C. et al "Quantification of Near-Field Heating During Volumetric MR_HIFU Ablation", Medical Physics, vol. 38, No. 1, Dec. 2010, pp. 272-282.

*Primary Examiner* — Ruth S Smith
(74) *Attorney, Agent, or Firm* — Intrinsic Law Corp.

(57) ABSTRACT

The invention provides for a medical instrument (200) comprising a magnetic resonance imaging system (202) and a high intensity focused ultrasound system (202) with an adjustable focus (238). Execution of instructions causes a processor to control (100) medical instrument to sonicate the multiple sonication points while repeatedly acquire the thermal magnetic resonance imaging data. Multiple thermal maps are reconstructed using the thermal magnetic resonance imaging data and a heating center of mass is calculated for each. By comparing each of the heating center of masses to the sonication points a spatially dependent targeting correction (266) is determined. The spatially dependent targeting correction is then used to offset the adjustable focus.

15 Claims, 5 Drawing Sheets

(51) Int. Cl.
*A61B 18/00* (2006.01)
*A61B 90/00* (2016.01)

(52) U.S. Cl.
CPC ............... *A61B 2018/00577* (2013.01); *A61B 2018/00738* (2013.01); *A61B 2018/00791* (2013.01); *A61B 2018/00898* (2013.01); *A61B 2018/00988* (2013.01); *A61B 2090/374* (2016.02); *A61N 2007/0086* (2013.01)

(58) Field of Classification Search
CPC .... A61B 2018/00988; A61B 2090/374; A61B 5/015; A61B 5/055; A61N 2007/0086; A61N 7/00; A61N 7/02
See application file for complete search history.

(56) References Cited

U.S. PATENT DOCUMENTS

| | | |
|---|---|---|
| 7,871,406 B2 | 1/2011 | Nields |
| 8,068,894 B2 | 11/2011 | Huizenga et al. |
| 2005/0065429 A1 | 3/2005 | Zhou |
| 2011/0251607 A1 | 10/2011 | Kruecker |

FOREIGN PATENT DOCUMENTS

| | | |
|---|---|---|
| JP | 6315541 A | 11/1994 |
| JP | 0747079 A | 2/1995 |
| JP | 884740 A | 4/1996 |
| WO | 200243804 A1 | 6/2002 |
| WO | 2011080631 A2 | 7/2011 |

FIG. 3

HIGH INTENSITY FOCUSED ULTRASOUND TARGETING

CROSS-REFERENCE TO PRIOR APPLICATIONS

This application is the U.S. National Phase application under 35 U.S.C. § 371 of International Application No. PCT/IB2013/055091, filed on Jun. 21, 2013, which claims the benefit of European Patent Application No. 12172873.7, filed on Jun. 21, 2012. These applications are hereby incorporated by reference herein.

TECHNICAL FIELD

The invention relates to high intensity focused ultrasound, in particular to the use of magnetic resonance thermometry to improve ultrasound targeting.

BACKGROUND OF THE INVENTION

In high intensity focused ultrasound (HIFU) an array of ultrasonic transducer elements are used to form an ultrasonic transducer. Supplying alternating current electrical power to the transducer elements causes them to generate ultrasonic waves. The ultrasonic waves from each of the transducer elements either add constructively or destructively at different locations in the beam path. By controlling the phase of alternating current electrical power supplied to each of the transducer elements the focal point or volume into which the ultrasound power is focused may be controlled.

High-intensity focused ultrasound (HIFU) therapy of tumors requires a high degree of spatial accuracy in order to avoid damaging healthy tissue as well as to obtain optimal usage of the system. Although avoiding damaging healthy tissue due to poor targeting is typically not a problem for large stationary tumors if utilizing low-power test sonications as is current practice, the technical performance and/or clinical performance of the system may suffer if incorrect positional knowledge is used for a feedback algorithm for example. This translates into reduced treatment efficiency.

The European patent application EP 0627 206 discloses an ultrasound medical treatment system which spatially resolves the hot spot and prevents displacement of the hot spot form the focal point of the ultrasound beam. The hot spot is resolved on the basis of an energy irradiation at a prescribed level lower than that of a treatment energy irradiation.

SUMMARY OF THE INVENTION

The invention provides for a medical instrument, a computer program product and a method in the independent claims. Embodiments are given in the dependent claims.

As will be appreciated by one skilled in the art, aspects of the present invention may be embodied as a apparatus, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer executable code embodied thereon.

Any combination of one or more computer readable medium(s) may be utilized. The computer readable medium may be a computer readable signal medium or a computer readable storage medium. A 'computer-readable storage medium' as used herein encompasses any tangible storage medium which may store instructions which are executable by a processor of a computing device. The computer-readable storage medium may be referred to as a computer-readable non-transitory storage medium. The computer-readable storage medium may also be referred to as a tangible computer readable medium. In some embodiments, a computer-readable storage medium may also be able to store data which is able to be accessed by the processor of the computing device. Examples of computer-readable storage media include, but are not limited to: a floppy disk, a magnetic hard disk drive, a solid state hard disk, flash memory, a USB thumb drive, Random Access Memory (RAM), Read Only Memory (ROM), an optical disk, a magneto-optical disk, and the register file of the processor. Examples of optical disks include Compact Disks (CD) and Digital Versatile Disks (DVD), for example CD-ROM, CD-RW, CD-R, DVD-ROM, DVD-RW, or DVD-R disks. The term computer readable-storage medium also refers to various types of recording media capable of being accessed by the computer device via a network or communication link. For example a data may be retrieved over a modem, over the internet, or over a local area network. Computer executable code embodied on a computer readable medium may be transmitted using any appropriate medium, including but not limited to wireless, wireline, optical fiber cable, RF, etc., or any suitable combination of the foregoing.

A computer readable signal medium may include a propagated data signal with computer executable code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

'Computer memory' or 'memory' is an example of a computer-readable storage medium. Computer memory is any memory which is directly accessible to a processor. 'Computer storage' or 'storage' is a further example of a computer-readable storage medium. Computer storage is any non-volatile computer-readable storage medium. In some embodiments computer storage may also be computer memory or vice versa.

A 'processor' as used herein encompasses an electronic component which is able to execute a program or machine executable instruction or computer executable code. References to the computing device comprising "a processor" should be interpreted as possibly containing more than one processor or processing core. The processor may for instance be a multi-core processor. A processor may also refer to a collection of processors within a single computer system or distributed amongst multiple computer systems. The term computing device should also be interpreted to possibly refer to a collection or network of computing devices each comprising a processor or processors. The computer executable code may be executed by multiple processors that may be within the same computing device or which may even be distributed across multiple computing devices.

Computer executable code may comprise machine executable instructions or a program which causes a processor to perform an aspect of the present invention. Computer executable code for carrying out operations for aspects of the present invention may be written in any combination of one or more programming languages, including an object oriented programming language such as Java, Smalltalk, C++ or the like and conventional procedural programming languages, such as the "C" programming language or similar programming languages and compiled into machine executable instructions. In some instances the computer executable code may be in the form of a high level language or in a pre-compiled form and be used in conjunction with an interpreter which generates the machine executable instructions on the fly.

The computer executable code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block or a portion of the blocks of the flowchart, illustrations, and/or block diagrams, can be implemented by computer program instructions in form of computer executable code when applicable. It is further under stood that, when not mutually exclusive, combinations of blocks in different flowcharts, illustrations, and/or block diagrams may be combined. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

A 'user interface' as used herein is an interface which allows a user or operator to interact with a computer or computer system. A 'user interface' may also be referred to as a 'human interface device.' A user interface may provide information or data to the operator and/or receive information or data from the operator. A user interface may enable input from an operator to be received by the computer and may provide output to the user from the computer. In other words, the user interface may allow an operator to control or manipulate a computer and the interface may allow the computer indicate the effects of the operator's control or manipulation. The display of data or information on a display or a graphical user interface is an example of providing information to an operator. The receiving of data through a keyboard, mouse, trackball, touchpad, pointing stick, graphics tablet, joystick, gamepad, webcam, headset, gear sticks, steering wheel, pedals, wired glove, dance pad, remote control, and accelerometer are all examples of user interface components which enable the receiving of information or data from an operator.

A 'hardware interface' as used herein encompasses an interface which enables the processor of a computer system to interact with and/or control an external computing device and/or apparatus. A hardware interface may allow a processor to send control signals or instructions to an external computing device and/or apparatus. A hardware interface may also enable a processor to exchange data with an external computing device and/or apparatus. Examples of a hardware interface include, but are not limited to: a universal serial bus, IEEE 1394 port, parallel port, IEEE 1284 port, serial port, RS-232 port, IEEE-488 port, Bluetooth connection, Wireless local area network connection, TCP/IP connection, Ethernet connection, control voltage interface, MIDI interface, analog input interface, and digital input interface.

A 'display' or 'display device' as used herein encompasses an output device or a user interface adapted for displaying images or data. A display may output visual, audio, and or tactile data. Examples of a display include, but are not limited to: a computer monitor, a television screen, a touch screen, tactile electronic display, Braille screen, Cathode ray tube (CRT), Storage tube, Bistable display, Electronic paper, Vector display, Flat panel display, Vacuum fluorescent display (VF), Light-emitting diode (LED) displays, Electroluminescent display (ELD), Plasma display panels (PDP), Liquid crystal display (LCD), Organic light-emitting diode displays (OLED), a projector, and Head-mounted display.

Medical image data is defined herein as two or three dimensional data that has been acquired using a medical imaging scanner. A medical imaging scanner is defined herein as a apparatus adapted for acquiring information about the physical structure of a patient and construct sets of two dimensional or three dimensional medical image data. Medical image data can be used to construct visualizations which are useful for diagnosis by a physician. This visualization can be performed using a computer.

Magnetic Resonance (MR) data is defined herein as being the recorded measurements of radio frequency signals emitted by atomic spins by the antenna of a Magnetic resonance apparatus during a magnetic resonance imaging scan. Magnetic resonance data is an example of medical image data. A Magnetic Resonance Imaging (MRI) image is defined herein as being the reconstructed two or three dimensional visualization of anatomic data contained within the magnetic resonance imaging data. This visualization can be performed using a computer.

Magnetic resonance data may comprise the measurements of radio frequency signals emitted by atomic spins by the antenna of a Magnetic resonance apparatus during a magnetic resonance imaging scan which contains information which may be used for magnetic resonance thermometry. Magnetic resonance thermometry functions by measuring changes in temperature sensitive parameters. Examples of parameters that may be measured during magnetic resonance thermometry are: the proton resonance frequency shift, the diffusion coefficient, or changes in the T1 and/or T2 relaxation time may be used to measure the temperature using magnetic resonance. The proton resonance frequency shift is temperature dependent, because the magnetic field that individual protons, hydrogen atoms, experience depends upon the surrounding molecular structure. An increase in temperature decreases molecular screening due to the temperature affecting the hydrogen bonds. This leads to a temperature dependence of the proton resonance frequency.

The proton density depends linearly on the equilibrium magnetization. It is therefore possible to determine temperature changes using proton density weighted images.

The relaxation times T1, T2, and T2-star (sometimes written as T2*) are also temperature dependent. The reconstruction of T1, T2, and T2-star weighted images can therefore be used to construct thermal or temperature maps.

The temperature also affects the Brownian motion of molecules in an aqueous solution. Therefore pulse sequences which are able to measure diffusion coefficients such as a pulsed diffusion gradient spin echo may be used to measure temperature.

One of the most useful methods of measuring temperature using magnetic resonance is by measuring the proton resonance frequency (PRF) shift of water protons. The resonance frequency of the protons is temperature dependent. As the temperature changes in a voxel the frequency shift will cause the measured phase of the water protons to change. The temperature change between two phase images can therefore be determined. This method of determining temperature has the advantage that it is relatively fast in comparison to the other methods. The PRF method is discussed in greater detail than other methods herein. However, the methods and techniques discussed herein are also applicable to the other methods of performing thermometry with magnetic resonance imaging.

Spectroscopic magnetic resonance data is defined herein as being the recorded measurements of radio frequency signals emitted by atomic spins by the antenna of a Magnetic resonance apparatus during a magnetic resonance imaging scan which contains information which is descriptive of multiple resonance peaks.

The spectroscopic magnetic resonance data may for instance be used to perform a proton spectroscopic (PS) imaging based temperature mapping method which can produce temperature maps on absolute scale. This absolute scale temperature map may therefore be used to perform a temperature calibration. This method relies on the physical principles of water proton resonance shift temperature dependence as the proton resonance frequency method, but the acquisition method is different: the frequency shift is calculated from the magnetic resonance spectra. The shift is calculated from the position difference of the water and a reference proton peak. Protons in lipids may for example be used as reference, as their resonance frequency is known to be almost independent of temperature, while the water proton peak has linear dependence on temperature. This can be done in the voxels, where both tissue types are present. If water and lipids do not exist in the same voxel, one may try to use some other tissue type than lipids as reference. If not successful, there may be some voxels where the reference peaks, and therefore the temperature data, are not available. Interpolation and/or temperature filtering may be used to help these situations, since body temperature is normally not expected to change rapidly spatially with the highly localized temperature rise typically caused by thermal therapy being an obvious exception. The utilization of reference peaks makes the method relatively independent of field drifts or inter-scan motion. Because the scanning takes a time of at least on the order of one minute with current methods, the PS method is susceptible to intra-scan motion or temperature change during scanning. In a case where temperature is constant or temperature variation is small both in time and space, the method is able to produce useful information. For example, with the Magnetic Resonance Guided High Intensity Focused Ultrasound (MR-HIFU), the PS method can be used to provide the actual body temperature distribution before start of MR-HIFU or other temperature treatment as opposed to using a spatially homogeneous starting temperature taken as the body core temperature measured with a thermometer probe. Alternatively, the PS method can be used as a sanity check for the cumulative temperature between heat treatments outside the treatment area.

An 'ultrasound window' as used herein encompasses a window which is effectively transparent to ultrasonic waves or energy. Typically a thin film or membrane is used as an ultrasound window. The ultrasound window may for example be made of a thin membrane of BoPET (Biaxially-oriented polyethylene terephthalate).

In one aspect the invention provides for a medical instrument comprising a magnetic resonance imaging system for acquiring thermal magnetic resonance data from a subject. The subject is at least partially located within the imaging zone. The medical instrument further comprises a high-intensity focused ultrasound system. The high-intensity focused ultrasound system has an adjustable focus. The high-intensity focused ultrasound system is operable for controlling the adjustable focus to sonicate the subject at multiple sonication points within the imaging zone. These multiple sonications each involve deposition of an amount of ultrasound energy that affects the local structure or physiology of the tissue into which the ultrasound energy is deposited. For example, the local structure may be affected in that ablation occurs or that hyperthermic physiologic effects are generated. Generally, these multiple sonications are carried-out at an ultrasound energy or intensity above a therapeutic threshold. The therapeutic threshold is set such that at ultrasound energy, intensity or accumulated thermal dose is below the therapeutic threshold only a temperature rise of the tissue arises with no or no significant physiological effect. The adjustable focus could be adjustable in more than one way. In some embodiments the high-intensity focused ultrasound transducer comprises a transducer which is able to be repositioned in different positions. In this way the focus is adjustable. In other embodiments, also including those of the previous ones with the transducer that is moveable, the transducer has multiple transducer elements which are able to have the phase and/or amplitude of electrical power supplied to them controlled. This allows the focus to be controlled electronically.

The medical instrument further comprises a processor for controlling the high-intensity focused ultrasound system and the magnetic resonance imaging system. The medical instrument further comprises a memory for storing machine-executable instructions for execution by the processor. Execution of the instructions causes the processor to control the high-intensity focused ultrasound system to sequentially sonicate multiple sonication points. The high-intensity focused ultrasound system is operable for controlling the adjustable focus to sonicate the subject at the multiple sonication points within the imaging zone. Execution of the instructions further cause the processor to control the magnetic resonance imaging system to repeatedly acquire the thermal magnetic resonance imaging data. The magnetic resonance imaging system acquires the thermal magnetic resonance imaging data at different times during the process of sonicating the multiple sonication points.

Execution of the instructions further causes the processor to repeatedly reconstruct multiple thermal maps using the thermal magnetic resonance imaging data. A thermal map as used herein encompasses a map descriptive of the heating of the subject. This may for instance be a temperature map at a particular time or it may also be an accumulated thermal dose. Execution of the instructions further cause the processor to calculate a heating center of mass for each of the multiple thermal maps creating a set of heating center of masses. A heating center of mass as used herein is a location to which heat may be added to reproduce the effect descriptive in the multiple thermal map. For instance a heating center of mass may be a particular or actual sonication point where heat is added to a subject.

Execution of the instructions further cause the processor to select one or more sonication points from the multiple sonication points for each member of the set of heating center of masses. The one or more sonication points are selected such that the high-intensity focused ultrasound system sonicates the one or more sonication points within a predetermined time prior to acquisition of the thermal magnetic resonance imaging data corresponding to the heating center of mass. Another way of saying that the thermal magnetic resonance imaging data corresponds to the heating center of mass is that a particular heating center of mass was determined using a particular acquisition of the thermal magnetic resonance imaging data.

In other words the thermal magnetic resonance data is acquired and used to construct thermal maps. The sonication points which were acquired prior to the acquisition of the thermal magnetic resonance imaging data are used or selected for an analysis to determine the accuracy of the targeting.

Execution of the instructions further cause the processor to determine a spatially-dependent targeting correction by comparing each member of the set of the heating centers of masses to the one or more sonication points. The actual thermal map or measured temperature data is then compared to the location of the sonication points. By making this comparison it can be determined that there may be an offset between the desired location of the sonication point and the actual location where heat is added to the subject. One way of making the comparison is to determine a location of a heating center of mass and then determining a location of a sonication point or sonication points. The difference between these the heating center of mass and the sonication point or points gives a displacement which may be used to calculate a spatially dependent targeting correction.

Execution of the instructions further cause the processor to control the high-intensity focused ultrasound system to offset the adjustable focus by the spatially-dependent targeting correction. This embodiment may be beneficial because it may lead to more accurate targeting of the high-intensity focused ultrasound system.

In another embodiment execution of the instructions further cause the processor to determine a time-dependent thermal dose distribution using the multiple thermal maps. The set of heating center of masses are calculated by searching for at least one maximum in the thermal dose distribution. Looking for the maximum in the thermal dose distribution the maximum heating effect of the sonication point may be determined. This may be used to more accurately target the high-intensity focused ultrasound system. It should be noted that the different maximums are obtained at different times when examining the time-dependent thermal dose distribution. These maximums are then related to the sonication points. In some embodiments the time-dependent thermal dose distribution is a cumulative thermal dose distribution. In other embodiments the time-dependent thermal dose distribution is not cumulative. The time-dependent thermal dose distribution may be for a specific time interval, for instance the time when the sonication point or points which the maximum is being compared to were performed.

In another embodiment execution of the instructions further causes the processor to determine the spatially-dependent targeting correction by comparing a time-dependent translation of the at least one maximum to the sequence of the multiple sonication points. In this embodiment the way in which the maximum moves is compared to the location of the sonication points. This may be used to determine if the targeting of the high-intensity focused ultrasound system is accurate or not.

In another embodiment the high-intensity focused ultrasound system comprises an ultrasound transducer with a mechanical positioning system. The adjustable focus is at least partially offset by the spatially-dependent targeting correction by actuating the mechanical positioning system. This embodiment may be beneficial because the mechanical system can accurately compensate for an offset in the targeting of the high-intensity focused ultrasound system.

In another embodiment the adjustable focus is at least partially electronically controllable. The adjustable focus is at least partially offset by controlling the adjustable focus electronically. In this embodiment the high-intensity focused ultrasound system comprises a transducer which comprises multiple transducer elements. The electronically controllable refers to the fact that the phase and/or amplitude of electrical power or current supplied to the individual transducer elements may be used to control the constructive and/or destructive interference of ultrasound generated by the individual transducer elements. By controlling the phase and/or amplitude this enables the electronic steering of the location of the adjustable focus.

In another embodiment execution of the instructions further causes the processor to control the high-intensity focused ultrasound system to offset the adjustable focus by the spatially-dependent targeting correction concurrently with controlling the high-intensity focused ultrasound system to sequentially sonicate the multiple sonication points. This embodiment is beneficial because it enables the correction of the targeting location on the fly. As the various sonication points of the subject are sonicated the targeting or control of the adjustable focus becomes more accurate the longer the device is used.

In another embodiment execution of the instructions further causes the processor to control the high-intensity focused ultrasound system to offset the adjustable focus after a predetermined number of the multiple sonication points have been sonicated. In this embodiment after a predetermined number of the sonication points have been sonicated the spatially-dependent targeting correction is used to correct the focusing of the high-intensity focused ultrasound system. This may lead to more accurate focusing of the high-intensity focused ultrasound system.

In another embodiment execution of the instructions further causes the processor to calculate a focus correction for the multiple sonication points not yet sonicated using the time-dependent thermal dose distribution and an ultrasound model. The sonic properties of tissue locations which have been previously sonicated may change. For instance a tissue that has been sonicated typically absorbs ultrasound more readily than tissue which has not already been sonicated. In these instances the use of an ultrasound model may allow for a more accurate prediction of where the ultrasound energy will be deposited within a subject.

In another embodiment execution of the instructions further causes the processor to generate a warning message if the focus correction is larger than a predetermined value. This may be useful in the situation where an effect causes the focus to occur at a location that is shifted from the intended sonication location. This may possibly be in a direction that is away from the ablated region when looked at perpendicularly to the beam axis. A ray tracing algorithm or other technique may be useful for this.

In another embodiment execution of the instructions further causes the processor to store the spatially-dependent targeting correction in the memory for use in a future sonication. For instance the targeting correction could be stored and used for the same subject later or for another subject.

In another embodiment the spatially-dependent targeting correction is determined by performing a polynomial fit to the thermal dose and to the multiple sonication points. In some embodiments the spatially-dependent targeting correction may be determined by performing a polynomial fit to increase the accuracy of the targeting correction.

In another embodiment the predetermined criterion is that the high intensity focused ultrasound system sonicates the one or more sonication points within a predetermined time prior to acquisition of the thermal magnetic resonance imaging data corresponding to the heating center of mass.

In another embodiment the predetermined criterion is excluding sonication points outside of a predetermined distance of the heating center of mass, In another embodiment the predetermined criterion is selecting sonication points using a fit determined by the spatially dependent targeting correction, In another embodiment the predetermined criterion is selecting the one or more sonication points using a neighbor fit determined by the spatially dependent targeting correction of other sonication points within a predetermined neighbor distance of the one or more sonication points.

In another aspect the invention provides for a computer program product comprising machine-executable instructions for execution by a processor controlling a medical instrument. The medical instrument comprises a magnetic resonance imaging system for acquiring thermal magnetic resonance data from a subject. The subject may be at least partially located within the imaging zone of the magnetic resonance imaging system. The medical instrument further comprises a high-intensity focused ultrasound system. The high-intensity focused ultrasound system has an adjustable focus. The high-intensity focused ultrasound system is operable for controlling the adjustable focus to sonicate the subject at multiple sonication points within the imaging zone.

Execution of the instructions further causes the processor to control the high-intensity focused ultrasound system to sequentially sonicate the multiple sonication points. Execution of the instructions further cause the processor to control the magnetic resonance imaging system to repeatedly acquire the thermal magnetic resonance imaging data. Execution of the instructions further causes the processor to reconstruct multiple thermal maps repeatedly using the thermal magnetic resonance imaging data.

Execution of the instructions further cause the processor to calculate a heating center of mass for each of the multiple thermal maps creating a set of heating center of masses. Execution of the instructions further cause the processor to select one or more sonication points from the multiple sonication points for each member of the set of heating center of masses. The one or more sonication points are selected such that the high-intensity focused ultrasound system sonicates the one or more location points within a predetermined time prior to acquisition of the thermal magnetic resonance imaging data corresponding to the heating center of mass.

Execution of the instructions further cause the processor to determine a spatially-dependent targeting correction by comparing each member of the set of the heating center of masses to the one or more sonication points. Execution of the instructions further cause the processor to control the high-intensity focused ultrasound system to offset the adjustable focus by the spatially-dependent targeting correction.

In another embodiment execution of the instructions further cause the processor to determine a time-dependent thermal dose distribution using the multiple thermal maps. The set of heating center of masses are calculated by searching for at least one maximum in the thermal dose distribution.

In another embodiment execution of the instructions further causes the processor to determine the spatially-dependent targeting correction by comparing a time-dependent translation of the at least one maximum to the sequence of the multiple sonication points.

In another aspect the invention provides for a method for controlling a medical instrument. The medical instrument comprises a magnetic resonance imaging system for acquiring thermal magnetic resonance data from a subject at least partially located within the imaging zone of the medical instrument. The medical instrument further comprises a high-intensity focused ultrasound system. The high-intensity focused ultrasound system has an adjustable focus. The high-intensity focused ultrasound system is operable for controlling the adjustable focus to sonicate the subject at multiple sonication points within the imaging zone. The method comprises the step of controlling the high-intensity focused ultrasound system to sequentially sonicate the multiple sonication points. The method further comprises the step of controlling the magnetic resonance imaging system to repeatedly acquire the thermal magnetic resonance imaging data. The magnetic resonance imaging system is controlled to acquire the thermal magnetic resonance imaging data at different time points during the process or times when the high-intensity focused ultrasound system is sequentially sonicating the multiple sonication points.

The method further comprises the step of reconstructing multiple thermal maps repeatedly using the thermal magnetic resonance imaging data. The method further comprises the step of calculating a heating center of mass for each of the multiple thermal maps creating a set of heating center of masses. The method further comprises the step of selecting one or more sonication points from the multiple sonication points for each member of the set of heating center of masses. The one or more sonication points are selected such that the high-intensity focused ultrasound system sonicates the one or more sonication points within a predetermined time prior to acquisition of the thermal magnetic resonance imaging data corresponding to the heating center of mass.

The method further comprises the step of determining a spatially-dependent targeting correction by comparing each member of the set of the heating center of masses to the one or more sonication points. The method further comprises the step of controlling the high-intensity focused ultrasound system to offset the adjustable focus by the spatially-dependent targeting correction.

It is understood that one or more of the aforementioned embodiments of the invention may be combined as long as the combined embodiments are not mutually exclusive.

BRIEF DESCRIPTION OF THE DRAWINGS

In the following preferred embodiments of the invention will be described, by way of example only, and with reference to the drawings in which.

DETAILED DESCRIPTION OF THE EMBODIMENTS

Like numbered elements in these figures are either equivalent elements or perform the same function. Elements which have been discussed previously will not necessarily be discussed in later figures if the function is equivalent.

Figure 1:
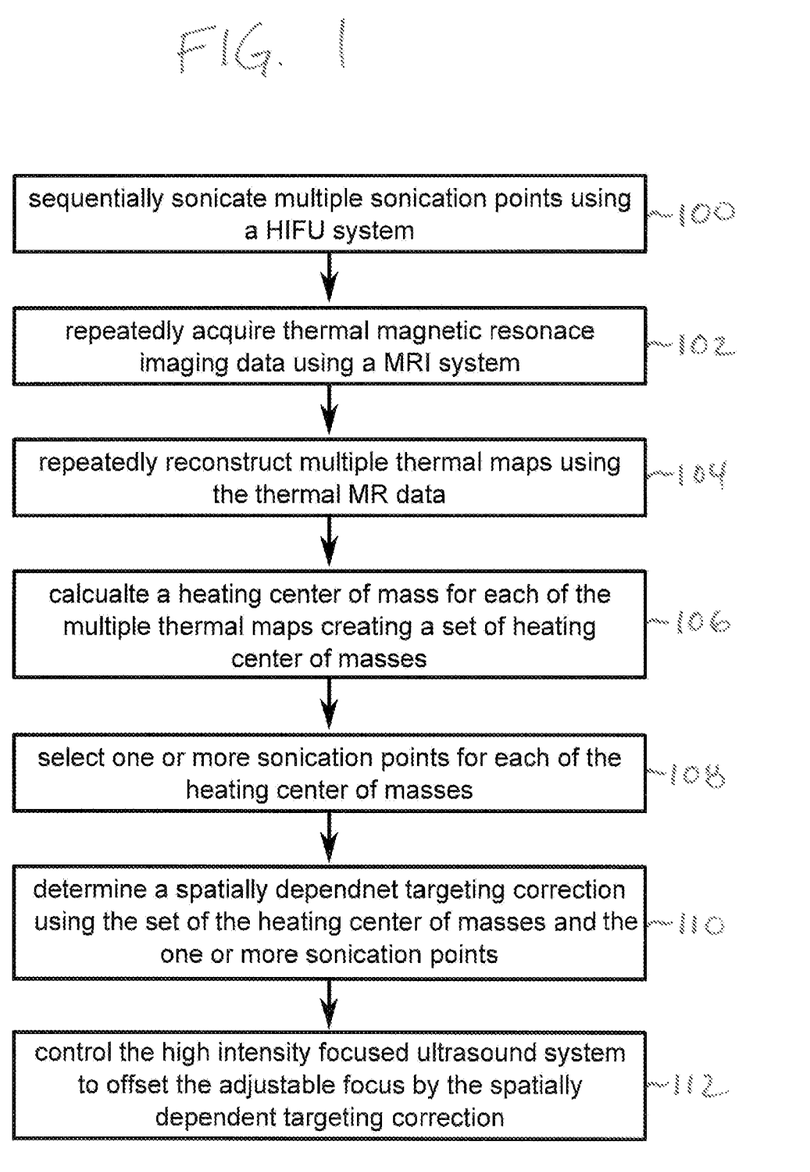
FIG. 1 shows a flowchart which illustrates a method according to an embodiment of the invention.

FIG. 1 shows a flowchart which illustrates a method according to an embodiment of the invention. In step 100 a high-intensity focused ultrasound system is used to sequentially sonicate multiple sonication points. Next in step 102 thermal magnetic resonance imaging data is acquired repeatedly using a magnetic resonance imaging system. The thermal magnetic resonance imaging data is acquired at different times during the sonication of the multiple sonication points. Next in step 104 multiple thermal maps are reconstructed repeatedly using the thermal magnetic resonance imaging data. Next in step 106 a heating center of mass is calculated for each of the multiple thermal maps creating a set of heating center of masses.

Then in step 108 one or more sonication points are selected for each of the heating center of masses. The one or more sonication points for each of the heating center of masses are selected such that the sonication is essentially responsible for the heating that is visible in the respective thermal map. Next in step 110 a spatially-dependent targeting correction is determined using the heating center of masses and the one or more sonication points. Finally in step 110 the high-intensity focused ultrasound system is controlled to offset the adjustable focus by the spatially-dependent targeting correction.

Figure 2:
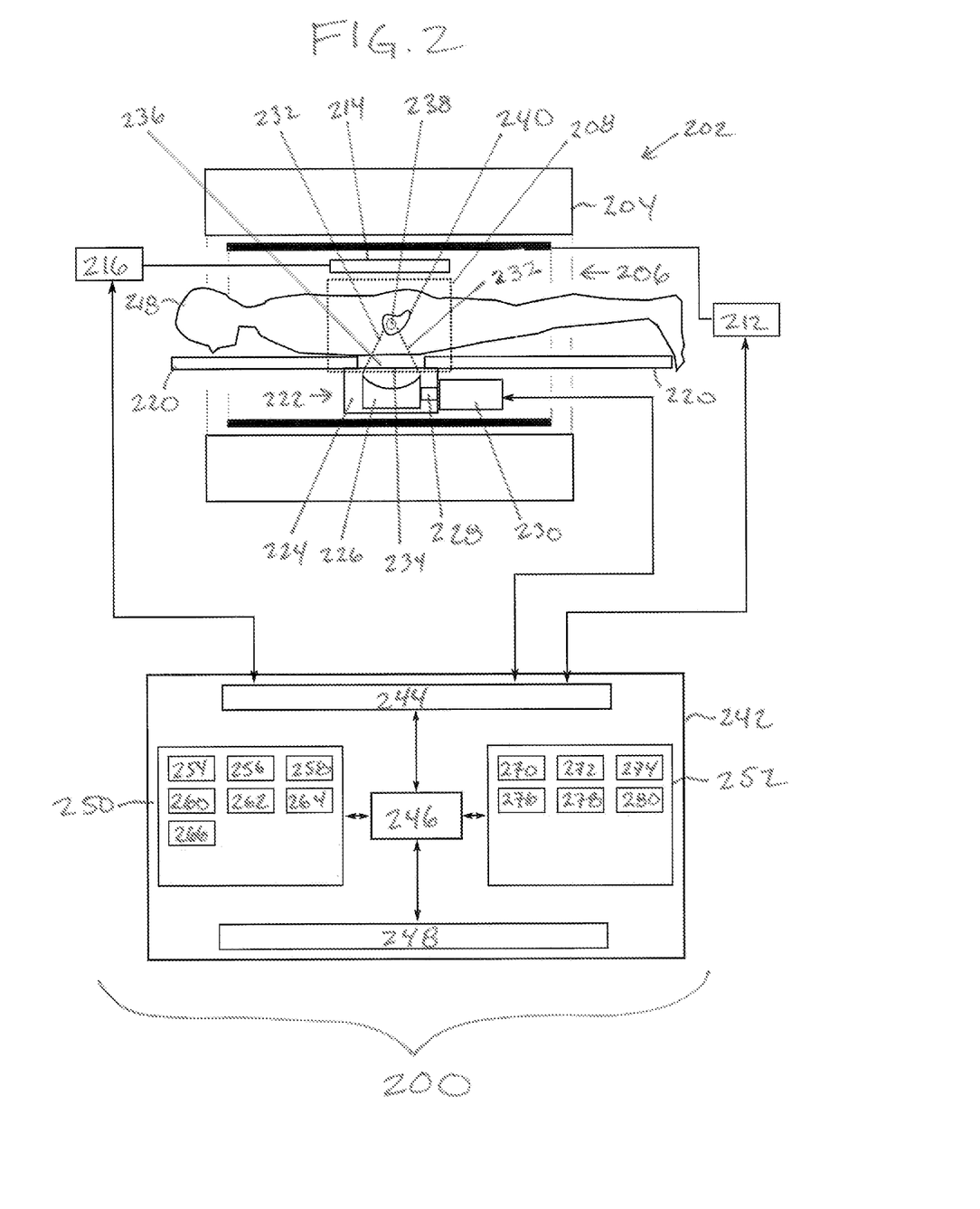
FIG. 2 illustrates a medical instrument according to an embodiment of the invention.

FIG. 2 shows a medical instrument 200 according to an embodiment of the invention. The medical instrument 200 comprises a magnetic resonance imaging system 202. The magnetic resonance imaging system comprises a magnet 204. The magnet 204 is a cylindrical type superconducting magnet with a bore 206 through the center of it. The magnet has a liquid helium cooled cryostat with superconducting coils. It is also possible to use permanent or resistive magnets. The use of different types of magnets is also possible for instance it is also possible to use both a split cylindrical magnet and a so called open magnet. A split cylindrical magnet is similar to a standard cylindrical magnet, except that the cryostat has been split into two sections to allow access to the iso-plane of the magnet, such magnets may for instance be used in conjunction with charged particle beam therapy. An open magnet has two magnet sections, one above the other with a space in-between that is large enough to receive a subject: the arrangement of the two sections area similar to that of a Helmholtz coil. Open magnets are popular, because the subject is less confined. Inside the cryostat of the cylindrical magnet there is a collection of superconducting coils. Within the bore 206 of the cylindrical magnet there is an imaging zone 308 where the magnetic field is strong and uniform enough to perform magnetic resonance imaging.

Within the bore 206 of the magnet there is also a set of magnetic field gradient coils 210 which are used for acquisition of magnetic resonance data to spatially encode magnetic spins within the imaging zone 208 of the magnet 204. The magnetic field gradient coils are connected to a magnetic field gradient coil power supply 212. The magnetic field gradient coils 210 are intended to be representative. Typically magnetic field gradient coils contain three separate sets of coils for spatially encoding in three orthogonal spatial directions. A magnetic field gradient power supply 212 supplies current to the magnetic field gradient coils 210. The current supplied to the magnetic field coils is controlled as a function of time and may be ramped or pulsed.

Adjacent to the imaging zone 208 is a radio-frequency coil 214 for manipulating the orientations of magnetic spins within the imaging zone 208 and for receiving radio transmissions from spins also within the imaging zone. The radio-frequency coil may contain multiple coil elements. The radio-frequency coil may also be referred to as a channel or an antenna. The radio-frequency coil 214 is connected to a radio frequency transceiver 216. The radio-frequency coil 214 and radio frequency transceiver 216 may be replaced by separate transmit and receive coils and a separate transmitter and receiver. It is understood that the radio-frequency coil 214 and the radio-frequency transceiver 216 are representative. The radio-frequency coil 214 is intended to also represent a dedicated transmit antenna and a dedicated receive antenna. Likewise the transceiver 216 may also represent a separate transmitter and receivers.

A subject 218 is shown as reposing on a subject support 220 and is located partially within the imaging zone 208. The medical instrument 200 also comprises a high-intensity focused ultrasound system 222. The high-intensity focused ultrasound system comprises a fluid-filled chamber 224. Within the fluid-filled chamber 224 is an ultrasound transducer 226. Although it is not shown in this figure the ultrasound transducer 226 may comprise multiple ultrasound transducer elements each capable of generating an individual beam of ultrasound. This may be used to steer the location of a sonication point 238 electronically by controlling the phase and/or amplitude of alternating electrical current supplied to each of the ultrasound transducer elements. Point 238 represents the adjustable focus of the medical instrument 200.

The ultrasound transducer 226 is connected to a mechanism 228 which allows the ultrasound transducer 226 to be repositioned mechanically. The mechanism 228 is connected to a mechanical actuator 230 which is adapted for actuating the mechanism 228. The mechanical actuator 230 also represents a power supply for supplying electrical power to the ultrasound transducer 226. In some embodiments the power supply may control the phase and/or amplitude of electrical power to individual ultrasound transducer elements. In some embodiments the mechanical actuator/power supply 230 is located outside of the bore 206 of the magnet 204.

The ultrasound transducer 226 generates ultrasound which is shown as following the path 232. The ultrasound 232 goes through the fluid-filled chamber 228 and through an ultrasound window 234. In this embodiment the ultrasound then passes through a gel pad 236. The gel pad 236 is not necessarily present in all embodiments but in this embodiment there is a recess in the subject support 220 for receiving a gel pad 236. The gel pad 236 helps couple ultrasonic power between the transducer 226 and the subject 218. After passing through the gel pad 236 the ultrasound 232 passes through the subject 218 and is focused to a sonication point 238. The sonication point 238 is being focused within a target volume 240. the target volume is determined by the sequence of the multiple sonication points. The sonication point 238 may be moved through a combination of mechanically positioning the ultrasonic transducer 226 and electronically steering the position of the sonication point 238 to treat the entire target volume 240.

The magnetic field gradient coil power supply 212, the transceiver 216, and the mechanical actuator/power supply 230 of the high-intensity focused ultrasound system 222 are shown as being connected to a hardware interface 244 of computer 242. The computer 242 further comprises a processor 246, a user interface 248, computer storage 250, and computer memory 2. The hardware interface 244 enables the processor 246 to send and receive commands and data in order to control the functioning of the medical instrument 200. The processor 246 is further connected to the user interface 248, the computer storage 250, and the computer memory 252.

The computer storage 250 is shown as containing a pulse sequence 254. The pulse sequence 254 either contains instructions or it contains a timeline which may be used for constructing constructions which enable the magnetic resonance imaging system 202 to acquire thermal magnetic resonance data 256. The computer storage 250 is shown as storing thermal magnetic resonance data 256 acquired by the magnetic resonance imaging system 202. The computer storage 250 is further shown as containing sonication points 258. The sonication points may for instance be stored in the form of a treatment plan or instructions for controlling the high-intensity focused ultrasound system 222. The sonication points 258 contain a sequence of locations to be sonicated by the high-intensity focused ultrasound system 222.

The computer storage 250 is further shown as containing thermal maps 260 which were reconstructed by a repeatedly acquired thermal magnetic resonance data 256. The computer storage 250 is further shown as containing a set of heating center of masses 262 that were calculated from the thermal maps 260. The computer storage 250 is further shown as containing selected sonication points 264. There are selected sonication points 264 which were selected from the sonication points 258 for each of the set of heating center of masses 262. The selected sonication points 264 were selected such that they were relevant to the heating or thermal dose which is evident in the particular thermal map 260. The computer storage 250 is further shown as containing a spatially-dependent targeting correction 266 that were calculated using the set of heating center of masses 262 and the corresponding selected sonication points 264.

The computer memory 252 is shown as containing a control module 270. The control module contains computer-executable code which enables the processor 246 to control the operation and function of the medical instrument 200. For example the control module 270 may use the pulse sequence 254 to acquire the thermal magnetic resonance data 256. The control module 270 may also use the sonication points 258 to sonicate the target volume 240. The computer memory 252 is shown as further containing a thermal map reconstruction module 272. The thermal map reconstruction module 272 contains computer-executable code which enables the processor 246 to reconstruct thermal maps 260 from the thermal magnetic resonance data 256. The computer memory 252 is further shown as containing a heating center of mass determination module 274. The heating center of mass determination module 274 contains computer-executable code which enables the processor 246 to determine the set of heating center of masses 262 from the thermal maps 260.

The computer memory 252 is shown as further containing a sonication point selection module 276. The sonication point selection module 276 is operable for selecting the sonication points 264 appropriate for each of the set of heating center of masses 262. The computer memory 252 is shown as further containing a spatially-dependent targeting correction determination module 278 which enables the processor 246 to calculate the spatially-dependent targeting correction 266 using the set of heating center of masses 262 and the selected sonication points 264. In its simplest embodiment the spatially-dependent targeting correction determination module 278 may simply fit a line or curve to targeting corrections determined at individual locations. The computer memory 252 is further shown as containing ultrasound focused correction module 280. The ultrasound focused correction module 280 is operable for modifying commands sent to the high-intensity focused ultrasound system 222 such that the spatially-dependent targeting correction determination is used when sonicating the subject 218.

In most ablative HIFU therapies, numerous sonication events are needed to ablate the target. In order for the treatment to be as safe and efficient as possible the ablated region by each individual sonication event should be as close in size and location to that intended. As an example, if the actually coagulated region is offset by (say) 5 mm in one direction this might cause a serious safety issue if a sensitive structure is located nearby. To reduce the probability of systematic effects on the misregistration such as robot positioning inaccuracies as well as first order effects of the beam path heterogeneity the current standard procedure is to use a low-power test sonication that induces a low non-lethal temperature from which the center of the heating can then be deduced. The transducer position can then be corrected accordingly as small offsets can be sufficiently well corrected by mechanical translation of the transducer.

However, if the induced temperature rise of the test-shot is too low, then the determined center of the heating is prone to disturbances induced by noise. Moreover, even if the correction is done correctly for the said sonication position in which the test sonication was performed, errors in sonication location will occur if the beam paths of the planned sonications differ sufficiently from each other. Commonly, the beam paths always differ and the variance in the beam paths merely determines the amplitude of the error in sonication location. Also, the acoustic and thermal properties vary as the treatment continues, with already ablated tissue within the target area displaying different tissue parameters than non-ablated tissue. If the acoustic waves of subsequent sonications pass through (either entirely or partially) these already ablated regions then the actual heated area will be misplaced from the intended ablation area of that sonication event. Hence, there are many reasons why the use of only a single test sonication is insufficient for high accuracy correction of the sonication position for all subsequent therapeutic sonications. This may affect the safety if sensitive structures are nearby, and most certainly affects the therapy efficacy as heating may be produced in non-intended areas that do not have the desired therapeutic effect. This in turn renders those sonications much less useful and additional time and heat energy is needed to fulfill the therapy as intended.

Embodiments of the invention may adaptively change the offset based on that seen in the previous ablations of that session. The position of an ablation can, for example, be taken to be the center of mass of the region where the thermal dose reaches a lethal level. The thermal dose is a temporal integral of the temperature and is often used as an estimate for the thermal damage with a level of 240 equivalent minutes at 43° C. often taken as the limit for cell death. If more than one slice (in particularly if some slices are perpendicular through the intended focal region) is used for MR imaging of the temperature rise then a 3D estimate of the center of mass of the ablated region can be obtained.

The thus obtained offset can be used to better correct for sonication location errors. This approach already inherently overcomes the first problem outlined above, which was that of an insufficient temperature rise as compared to the noise level. For a lethal ablation to occur, temperatures are typically in excess of at least 55° C. which is 18° C. above the body core temperature and thus easily discernible. For example using a thermal dose such as 240 EM dose area's center of mass may be more relevant than the temperature as this represents a more exact estimate of thermally damaged region. The use of a thermal dose and the method of calculating the thermal dose may be tissue specific. For example, 240 EM is usually used in skeletal muscle and also uterine fibroids. In other instances other thermal dose limits may be used.

In some tissues types, the damage may also be more of a temperature threshold effect in addition to the possibility of a thermal dose effect. For example, the rapid heating that occurs in ultrasound ablation may rapidly increase the thermal dose from a value far below the threshold to far above in a very short time, thereby closely mimicking a temperature threshold effect. In place of a thermal dose estimates of the cell damage due to rapid heating may also be therefore used to calculate a center of mass. The spatial dependencies of the sonication location errors are often induced by differences in the beam paths. In the case of for example uterine fibroid ablation, this in turn arises from differences in fat layer thickness as well as proximity to the border of the fibroid and myometrium as well as angle of incidence to the fat-layer to name the probably most predominant reasons. However, these effects on the wave propagation as a function of distance are not rapid and the error in sonication location typically remains within some 7 mm or so even within large fibroids. For HIFU therapies utilizing external transducers, the offset is predominantly in the beam-axis direction of the transducer, which is the anterior-posterior direction in fibroid therapy.

Figure 3:
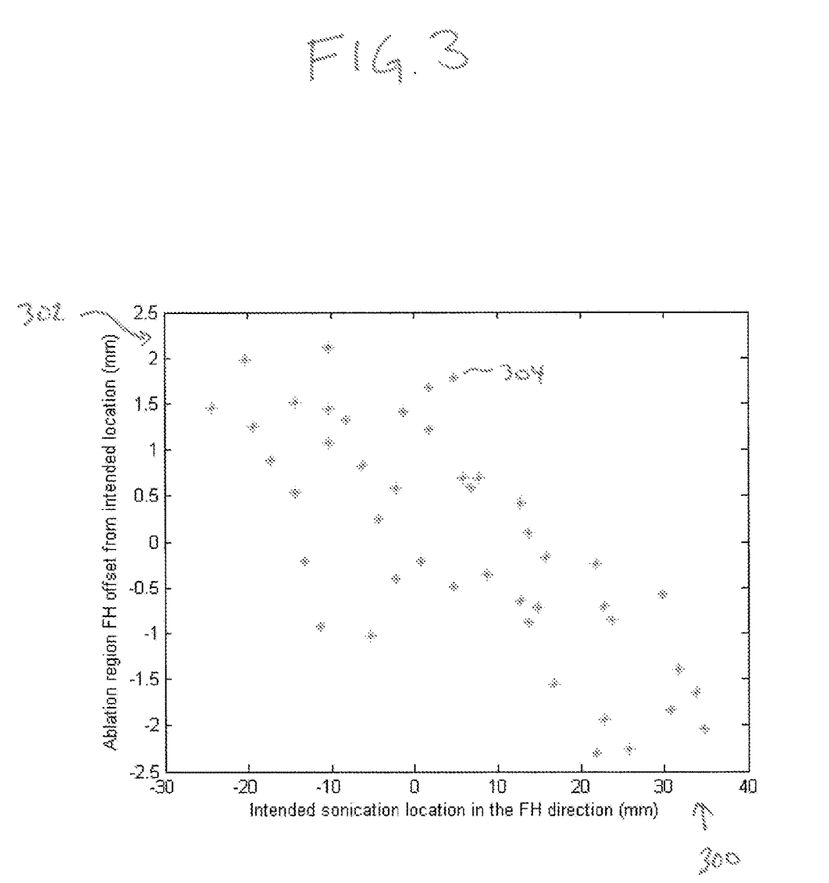
FIG. 3 plots the intended sonication location in the foot-to-head direction versus the actual sonication location in the foot-to-head direction.

FIG. 3 shows an example of the ablation CM (center of mass) offset from the intended sonication location as a function of the intended sonication location in the feet-head direction. In FIG. 3, the ablation location CM is offset in feet-head direction as a function of the treatment cell's position (i.e. intended sonication location) in the feet-head direction in one uterine fibroid. In this image a clear spatial dependency of the feet-head displacement can be seen as a function of the feet-head location of the intended sonication. In FIG. 3 the intended sonication location in the foot-to-head direction 300 is the x-axis and the offset of the actual sonication location from the intended location in the foot-to-head direction 302 is shown on the y-axis. Both locations are given in millimeters. The intended sonication location 300 corresponds to the set of sonication points and the actual sonication location 302 corresponds to the ablation region which is determined using the thermal maps. In this Fig. it can be seen that the offset from the intended location 302 shows a spatial dependence. FIG. 3 illustrates that a fit, either linear or with a polynomial or some other curve, may likely be used to increase the accuracy at which the sonication is targeted.

For ease of planning the intended sonications (called treatment cells in the Philips Sonalleve MR-HIFU platform), are often placed in one plane perpendicular to the transducer beam axis. This plane, here called a treatment plane, may or may not be tilted based on the angulation of the transducer. The reason for using planes in this direction is that the ablation regions are typically elongated in the direction of the beam axis for most external transducer and thereby anyways form a 3D ablated region. One could then perform a 2D spatial fit on the CM offset, for the AP (anterior posterior), LR (left right), and FH (foot head), of the ablation region induced by the already performed sonications within the treatment plane. One possibility is to do a 2D surface fit to the AP, LR, and FH ablation region offsets separately and then interpolate to the position of the upcoming sonication. This 3D position can then be used as an estimate for the likely sonication offset if no correction is performed, and thus be applied as a correction by mechanically translating the transducer accordingly. The CM values used for the fitting must be from the same frame of reference meaning that the mechanical correction applied for previous sonications may be removed in order for the fit to be on offset values that are comparative and only dependent on the intended sonication location. This idea can also be utilized for when no treatment planes are used by using a 3D fit instead. However, sonications using different degrees of transducer angulation although similar treatment cell center positions are not likely to cause a similar ablation location offset. In those cases, the different angulations should either be treated separately or added as additional dimensions to the fit.

The fit itself may be a polynomial of a sufficiently low order for the non-systematic effects (such as local minor tissue variability) not to have a too dominant impact. Other fits may also be used, but the amount of coefficients to be estimated must remain low and the function used should not have a too large derivative since the sonication location offsets do not change rapidly as a function of the displacement due to the tissue composition within the beam path only changing slowly with movement of the target.

Even though the differences in treatment cell location on the ablation offset are normally fairly slow since the tissue properties do not rapidly change as a function of position, this does not hold true if parts of the region are already ablated. Ablated areas may be very local and may furthermore have very different acoustic and thermal properties. First of all, perfusion is usually non-existent in ablated tissue, but the largest impact on the ablation location arises from the changes in ultrasound impedance and absorption induced in many tissues as a result of the ablation. As the tissue is ablated, proteins denature and the density of the tissue changes when the water distribution within the tissue is altered. This change in density causes a change in acoustic impedance, which in turn changes the wave propagation significantly. Large differences in impedance are known to cause partial reflections of the ultrasound waves. Whatever the actual cause, the ultrasound energy typically does not propagate as deep in recently ablated tissue as in functional non-ablated tissue. Since the ablated areas may be very localized, making a low-order polynomial fit will then be incorrect if including sonications made in already ablated regions. An alternative is to allow for a separate higher order polynomial fit in those regions, but this is not necessarily likely to be a robust approach. Moreover, the ablations that are planned in already ablated region are very likely to be displaced from their intended location.

In some cases, sonications may be intended to be so close to ablated regions that the ultrasound waves will partially need to propagate through already ablated regions. This is the more likely scenario. In such a case, the waves traversing the ablated tissue will be more reflected than the ones passing through in-tact tissue. This will in effect cause the focus to occur at a location that is shifted from the intended sonication location in a direction that is away from the ablated region when looked at perpendicularly to the beam axis. The shift may be significant and one means of dealing with this is to issue a warning to the user if the planned beam path intersects already ablated tissue. Another possible solution is to use ray tracing or some other acoustic simulation tool, to assess the level of distortion that is likely to occur.

Similar things can happen if the planned sonication is close to the border of the target, or goes through a significantly different beam path. For example, if a sonication is planned for the border in the LR/FH direction of a uterine fibroid, then more or less half of the ultrasound waves propagate through myometrium to reach the focus whereas the other half propagate through the uterine fibroid. The two tissues have different acoustic as well as thermal properties, which cause the realized sonication location to differ from those where most of the ultrasound waves all propagated mainly within the fibroid. The displacement will depend on the local spatial changes in the tissue properties and are not easy to assess. However, one solution might be to allow higher order corrections to be applied at the very borders of the target tissue, although this would require a high amount of observations to be reliable.

Usage of a spatial fit, for example a low order polynomial, in one to three dimensions may be used to assess and correct for the spatial offsets of the ablation region. The correction can be made by mechanically displacing the transducer accordingly. If large offsets are required to reach the desired accuracy, then the initial values should likely be dropped from the later fits as a mechanical linear displacement is not a valid estimate of the needed correction if the beam path is significantly changed due to a large offset correction. The ablation region offsets must be transformed into the same frame of reference for the fit to be valid (mechanical correction removed). For small offsets, electronic displacements may also be performed if a phased-array transducer is used. Acoustic simulation tools may be used to give further insight.

If already ablated tissue is within the beam path of a planned sonication, then a warning could be issued stating that the ablation is likely to be displaced. The amount of overlap of the beam path with the ablated region will affect the extent of displacement, and the direction of displacement will be away from the ablated region if the overlap occurs in the near-field of the beam path and only partially. This can be taken into account when ablating close to sensitive structures that are to be avoided. Acoustic simulation tools may be used to give further insight.

When very close to the edge of the target tissue, there may be more severe distortions in the beam shape than otherwise and a lower order polynomial fit may be insufficient. Higher order spatial fits may then be used towards the edges but this may be susceptible to errors. Acoustic simulation tools may also here be used.

Figure 4:
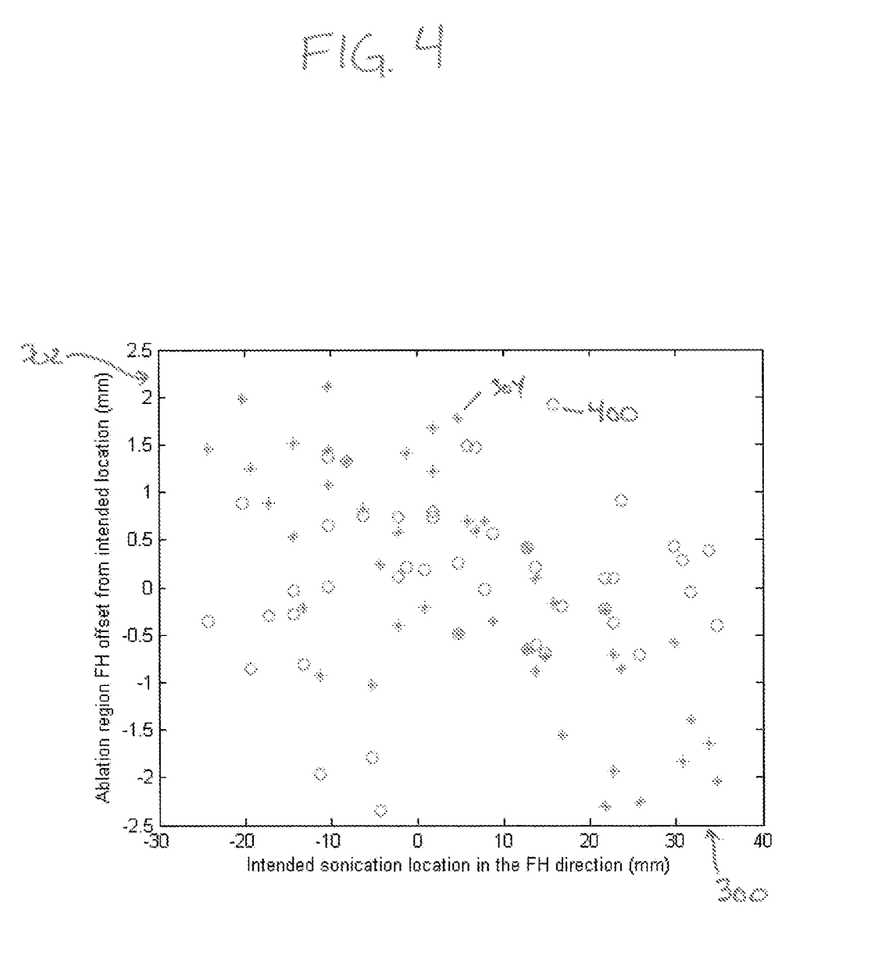
FIG. 4 shows the same plot as FIG. 3 with sonications using a corrected targeting additionally shown.

FIG. 4 shows how 1st order polynomial fit in two dimensions reduces the FH offset of the data shown in FIG. 3. In this case the uncorrected data 304 is marked with a star and corrected data is marked with a circle 400. The circles 400 indicate ablation locations offset in the foot-to-head direction as a function of the treatment cell's position after a 2-D first order polynomial fit was applied. It can be seen that the offset from the intended location is smaller than with the original set of data 304. This indicates how embodiments of the invention may be used to increase the targeting accuracy of a high-intensity focused ultrasound system. As with FIG. 3, FIG. 4 shows ablation locations CM offset in feet-head direction as a function of the treatment cell's position (i.e. intended sonication location) in the feet-head direction in one uterine fibroid before correction (blue stars) and after a 2D 1st order polynomial fit correction (red circles).

No correction was applied for the first 4 ablations during which only the test shot correction was applied. This was in order for the 3 coefficient fit to have sufficiently data for a reliable fit. An alternative would be to use a zeroth order correction for the very first ablations. Using the suggested correction strategy, the mean absolute FH offset was reduced from 1.08 mm to 0.65 mm in the remaining sonications for the case studied. The offsets are less dependent on local tissue differences perpendicular to the beam path, and higher polynomial orders may thus be used for those fits whereas even zeroth order corrections may be applied in the AP direction.

As a possible improvement, starting from the second sonication the offset found during the first ablation may be used as a zeroth order correction. Once the displacements are found to be above a certain threshold amplitude and a sufficient amount of sonications are performed to give statistical significance to the observed spatial dependence, then spatial fits may be introduced to further correct for the displacements. This is a more refined approach that is likely to yield improved corrections as compared to the approaches outlined above. This can be extended to test for higher order spatial correlations and then include these corrections if indeed the coefficients are found statistically significant at a given p-value for example. Higher order fits can also be added and actual importance of each coefficient re-estimated after each sonication if needed. The dependencies whose coefficients are shown not significant can be removed one by one, starting with the least important coefficient. This is one way to reduce the possibility of fitting to noise, i.e. local variances that do not aid explain the global behavior.

Figure 5:
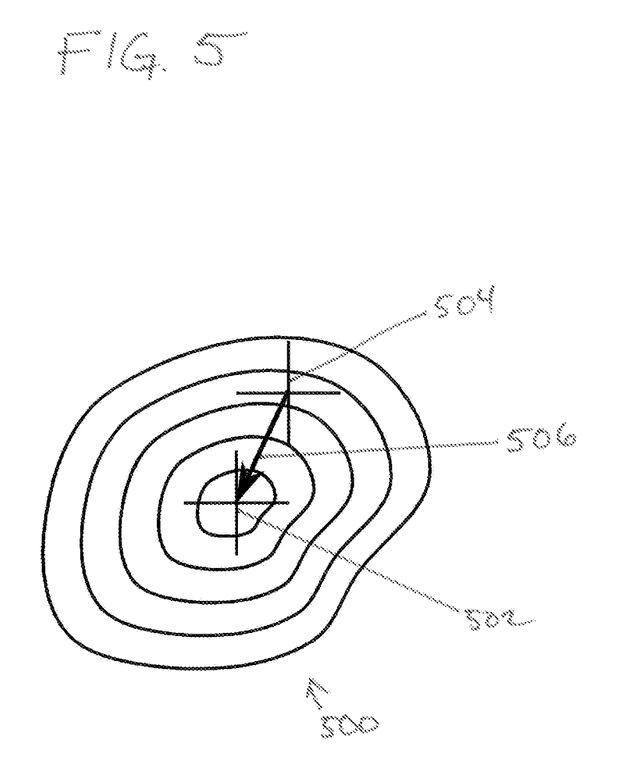
FIG. 5 illustrates a representation of a thermal map.

FIG. 5 illustrates a representation of a thermal map 500. The curves 500 represent either the curves of a temperature mapping or a thermal dose map. The cross 502 indicates a heating center of mass 502 indicated by the thermal map 500. Cross 504 indicates an intended sonication location 504. The arrow 506 illustrates a displacement from the heating center of mass from the sonication location 504. The displacement 506 using a group of or set of heating center of masses may be used to derive the spatially-dependent targeting correction.

While the invention has been illustrated and described in detail in the drawings and foregoing description, such illustration and description are to be considered illustrative or exemplary and not restrictive; the invention is not limited to the disclosed embodiments.

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measured cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A medical apparatus comprising:
   a magnetic resonance imaging system operable for acquiring thermal magnetic resonance data from a subject at least partially located within an imaging zone of the magnetic resonance imaging system;
   a high intensity focused ultrasound system wherein the high intensity focused ultrasound system has an adjustable focus, wherein the high intensity focused ultrasound system is operable for controlling the adjustable focus to sonicate the subject at multiple sonication points within the imaging zone;
   a processor for controlling the high intensity focused ultrasound system and the magnetic resonance imaging system;
   memory for storing machine executable instructions for execution by the processor, wherein execution of the instructions causes the processor to:
      control the high intensity focused ultrasound system to sequentially sonicate the multiple sonication points to exceed a therapeutic threshold;
      control the magnetic resonance imaging system to repeatedly acquire the thermal magnetic resonance imaging data;
      repeatedly reconstruct multiple thermal maps using the thermal magnetic resonance imaging data;
      calculate a heating center of mass for each of the multiple thermal maps creating a set of heating center of masses;
      selecting one or more sonication points from the multiple sonication points for each member of the set of heating center of masses, wherein the one or more sonication points are selected using a predetermined criterion;
      determine a spatially dependent targeting correction by comparing each member of the set of the heating center of masses to the one or more sonication points; and
      control the high intensity focused ultrasound system to offset the adjustable focus by the spatially dependent targeting correction.

2. The medical apparatus of claim 1, wherein execution of the instructions further causes the processor to determine a current offset of the focus based on offsets of previous sonications.

3. The medical apparatus of claim 1, wherein execution of the instructions further cause the processor to determine a time dependent thermal dose distribution using the multiple thermal maps, and wherein the set of heating center of masses are calculated by searching for at least one maximum in the thermal dose distribution.

4. The medical apparatus of claim 3, wherein execution of the instructions causes the processor to determine the spatially dependent targeting correction by comparing a time dependent translation of the at least one maximum to the sequence of the multiple sonication points.

5. The medical apparatus of claim 1, wherein the high intensity focused ultrasound system comprises an ultrasound transducer with a mechanical positioning system, and wherein the adjustable focus is at least partially offset by the spatially dependent targeting correction by actuating the mechanical positioning system.

6. The medical apparatus of claim 5, wherein execution of the instructions causes the processor to control the high intensity focused ultrasound system to offset the adjustable focus by the spatially dependent targeting correction concurrently with controlling the high intensity focused ultrasound system to sequentially sonicate the multiple sonication points.

7. The medical apparatus of claim 1, wherein the adjustable focus is at least partially electronically controllable, wherein the adjustable focus is at least partially offset by controlling the adjustable focus electronically.

8. The medical apparatus of claim 1, wherein execution of the instructions causes the processor to control the high intensity focused ultrasound system to offset the adjustable focus after a predetermined number of the multiple sonication points have been sonicated.

9. The medical apparatus of claim 8, wherein execution of the instructions further causes the processor to calculate a focus correction for the multiple sonication points not yet sonicated using a time dependent thermal dose distribution and an ultrasound model.

10. The medical apparatus of claim 9, wherein execution of the instructions further cause the processor to generate a warning message if the focus correction is larger than a predetermined value.

11. The medical apparatus of claim 1 wherein the spatially dependent targeting correction is determined by performing a polynomial fit to a thermal dose distribution and to the multiple sonication points.

12. The medical apparatus of claim 1, wherein the predetermined criterion is any one of the following: that the high intensity focused ultrasound system sonicates the one or more sonication points within a predetermined time prior to acquisition of the thermal magnetic resonance imaging data corresponding to the heating center of mass, excluding sonication points outside of a predetermined distance of the heating center of mass, selecting sonication points using a fit determined by the spatially dependent targeting correction, selecting the one or more sonication points using a neighbor fit determined by the spatially dependent targeting correction of other sonication points within a predetermined neighbor distance of the one or more sonication points, and combinations thereof.

13. A computer program product comprising a non-transitory computer readable medium storing machine executable instructions for execution by a processor controlling a medical apparatus comprising a magnetic resonance imaging system for acquiring thermal magnetic resonance data from a subject at least partially located within an imaging zone of the magnetic resonance imaging system, wherein the medical apparatus further comprises a high intensity focused ultrasound system, wherein the high intensity focused ultrasound system has an adjustable focus, wherein the high intensity focused ultrasound system is operable for controlling the adjustable focus to sonicate the subject at multiple sonication points within the imaging zone, wherein execution of the instructions causes the processor to:
control the high intensity focused ultrasound system to sequentially sonicate the multiple sonication points to exceed a therapeutic threshold;
control the magnetic resonance imaging system to repeatedly acquire the thermal magnetic resonance imaging data;
reconstruct multiple thermal maps repeatedly using the thermal magnetic resonance imaging data;
calculate a heating center of mass for each of the multiple thermal maps creating a set of heating center of masses;
selecting one or more sonication points from the multiple sonication points for each member of the set of heating center of masses, wherein the one or more sonication points are selected using a predetermined criterion;
determine a spatially dependent targeting correction by comparing each member of the set of the heating center of masses to the one or more sonication points; and
control the high intensity focused ultrasound system to offset the adjustable focus by the spatially dependent targeting correction.

14. The computer program product of claim 13, wherein execution of the instructions further cause the processor to determine a time dependent thermal dose distribution using the multiple thermal maps, and wherein the set of heating center of masses are calculated by searching for at least one maximum in the thermal dose distribution.

15. A method of controlling a medical apparatus, wherein the medical apparatus comprises a magnetic resonance imaging system for acquiring thermal magnetic resonance data from a subject at least partially located within an imaging zone magnetic resonance imaging system, wherein the medical apparatus further comprises a high intensity focused ultrasound system, wherein the high intensity focused ultrasound system has an adjustable focus, wherein the high intensity focused ultrasound system is operable for controlling the adjustable focus to sonicate the subject at multiple sonication points within the imaging zone, wherein the method comprises the steps of:
controlling the high intensity focused ultrasound system to sequentially sonicate the multiple sonication points to exceed a therapeutic threshold;
controlling the magnetic resonance imaging system to repeatedly acquire the thermal magnetic resonance imaging data;
reconstructing multiple thermal maps repeatedly using the thermal magnetic resonance imaging data;
calculating a heating center of mass for each of the multiple thermal maps creating a set of heating center of masses;
selecting one or more sonication points from the multiple sonication points for each member of the set of heating center of masses, wherein the one or more sonication points are selected using a predetermined criterion;
determining a spatially dependent targeting correction by comparing each member of the set of the heating center of masses to the one or more sonication points; and
controlling the high intensity focused ultrasound system to offset the adjustable focus by the spatially dependent targeting correction.

* * * * *